United States Patent
Verdu et al.

(10) Patent No.: US 10,849,845 B2
(45) Date of Patent: Dec. 1, 2020

(54) THICKENED, CLEAR SALT-RICH COMPOSITION, METHOD FOR LIGHTENING SAME, AND USE THEREOF IN COSMETICS

(71) Applicant: SOCIETE D'EXPLOITATION DE PRODUITS POUR LES INDUSTRIES CHIMIQUES SEPPIC, Paris (FR)

(72) Inventors: Benoît Verdu, Castres (FR); Cindy Sourdon, Verdalle (FR); Alicia Roso, Saïx (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 16/322,998

(22) PCT Filed: Jul. 18, 2017

(86) PCT No.: PCT/FR2017/051950
§ 371 (c)(1),
(2) Date: Feb. 4, 2019

(87) PCT Pub. No.: WO2018/024960
PCT Pub. Date: Feb. 8, 2018

(65) Prior Publication Data
US 2019/0183776 A1      Jun. 20, 2019

(30) Foreign Application Priority Data
Aug. 5, 2016 (FR) ...................... 16 57588

(51) Int. Cl.
| | | |
|---|---|---|
| A61K 8/81 | (2006.01) | |
| A61Q 19/00 | (2006.01) | |
| A61K 8/20 | (2006.01) | |
| A61Q 5/02 | (2006.01) | |
| A61Q 19/10 | (2006.01) | |
| A61K 8/39 | (2006.01) | |
| A61K 8/04 | (2006.01) | |
| A61K 8/19 | (2006.01) | |
| A61Q 5/00 | (2006.01) | |

(52) U.S. Cl.
CPC ............ *A61K 8/8194* (2013.01); *A61K 8/042* (2013.01); *A61K 8/19* (2013.01); *A61K 8/20* (2013.01); *A61K 8/39* (2013.01); *A61K 8/8158* (2013.01); *A61Q 5/00* (2013.01); *A61Q 5/02* (2013.01); *A61Q 19/00* (2013.01); *A61Q 19/10* (2013.01); *A61K 2800/48* (2013.01)

(58) Field of Classification Search
None
See application file for complete search history.

(56) References Cited

U.S. PATENT DOCUMENTS

| | | |
|---|---|---|
| 2,798,053 A | 7/1957 | Harold |
| 5,373,044 A | 12/1994 | Adams et al. |
| 6,645,476 B1 | 11/2003 | Morschhauser et al. |
| 2001/0029287 A1 | 10/2001 | Loffler et al. |
| 2005/0002977 A1 | 1/2005 | Mallo |
| 2012/0172457 A1 | 7/2012 | Braun et al. |
| 2014/0335039 A1 | 11/2014 | Merat |

FOREIGN PATENT DOCUMENTS

| | | |
|---|---|---|
| EP | 0 301 532 A2 | 2/1989 |
| EP | 0 816 403 A2 | 1/1998 |
| EP | 1 069 142 A1 | 1/2001 |
| EP | 1 116 733 A1 | 7/2001 |
| EP | 1 496 081 A1 | 1/2005 |
| FR | 2 910 899 A1 | 7/2008 |
| WO | 2011/030044 A1 | 3/2011 |

OTHER PUBLICATIONS

International Search Report, dated Oct. 23, 2017, from corresponding PCT/FR2017/051950 application.
FR Search Report, dated Dec. 15, 2016, from corresponding FR 1657588 application.

*Primary Examiner* — Sin J Lee
(74) *Attorney, Agent, or Firm* — Nixon & Vanderhye P.C.

(57) ABSTRACT

Disclosed is a composition including (per 100% weight): a) 90 wt.-% to 99.0 wt.-% water including, in dissolved form, 0.002 mol/L to 0.1 mol/L of at least one salt of ammonium cation or of a monovalent or multivalent metal cation with an organic or inorganic anion; b) 0.5 wt.-% to 5 wt.-% of a crosslinked anionic polyelectrolyte; and c) 0.5 wt.-% to 5 wt.-% of a compound having formula (II): $R_1$—(O—$CH_2$—$CH_2$)$_p$—OH (II), where the weight ratio of the crosslinked anionic polyelectrolyte to the compound of formula (II) is greater than or equal to 0.2 and less than or equal to 2.0, and the molar ratio of the compound of formula (II) to the salt greater than or equal to 0.05 and less than or equal to 1. Also disclosed is a composition in cosmetics and a method for lightening the thickened salt-rich composition.

18 Claims, No Drawings

THICKENED, CLEAR SALT-RICH COMPOSITION, METHOD FOR LIGHTENING SAME, AND USE THEREOF IN COSMETICS

The present invention relates to a novel thickened salt-rich hydrogel, to its use as a topical cosmetic composition and to a novel process for lightening a thickened salt-rich hydrogel.

Sera are widely used nowadays for cosmetic treatment of the skin. The term "serum" denotes aqueous solutions which are intended to be absorbed rapidly by the upper layers of the epidermis, and which contain a high concentration of active ingredients. They are generally used as a complement to various skincare formulations to increase the effect thereof: the skin is cleansed beforehand, and the serum is then applied, followed by the desired cosmetic care formulation. This process is particularly pertinent when the user observes that the effect of the care formulation is reduced, due to external factors such as the climatic or environmental conditions or in the event of a sudden change of state of the skin such as its dryness. Sera comprise substances that have various properties, such as moisturizing, lightening, purifying, antiaging, antiwrinkle, energizing, shadow-concealing and/or antisebum properties.

In order for sera to be easily and rapidly absorbed by the upper layers of the epidermis, they must have a non-greasy texture, having an equilibrium between flow characteristics that are fluid enough to enable rapid spreading over the surface of the skin to be treated, and gelled enough to avoid running at the time of application. Furthermore, it is preferred for the serum to be translucent since this aspect is associated by consumers with the notion of purity.

Synthetic polymers and polymers of natural origin are cosmetic aqueous-phase thickeners that are well known to those skilled in the art and that make it possible to prepare an aqueous gel for topical uses in the cosmetic and pharmaceutical fields.

The synthetic thickening polymers currently used in this field are in powder form or in liquid form as a water-in-oil emulsion of the polymer prepared by inverse emulsion radical polymerization using surfactants, commonly known as inverse latices.

Among the synthetic thickening polymers in powder form that are the most known, mention may be made of polymers based on acrylic acid and/or esters thereof such as those sold under the names Carbopol™ or Pemulen™. They are described especially in American U.S. Pat. Nos. 5,373,044 and 2,798,053 and also in European patent application EP 0 301 532 A2. There are also polymers based on 2-acrylamido-2-methylpropanesulfonic acid and/or salts thereof, such as those sold under the name Aristoflex™. They are described especially in European patents EP 0 816 403, EP 1 116 733 and EP 1 069 142. These powders are generally obtained by precipitating polymerization of the monomer(s) in solution in an organic solvent such as benzene, ethyl acetate, cyclohexane or tert-butanol; this process thus requires numerous successive steps for purification of the final product, to remove any trace of residual solvent.

Among the inverse latices that are the most known, mention may be made of those sold under the names Sepigel™, Simulgel™ and Sepiplus™. These thickeners are obtained by inverse emulsion radical polymerization. They are more readily manipulable, especially at room temperature, and disperse very rapidly in water. Furthermore, they develop remarkably high thickening performance qualities. However, since they contain an oil, this makes them potentially less pertinent for preparing translucent or transparent aqueous gels.

Synthetic thickeners also exist which have thickening performance qualities equivalent or superior to those of inverse latices, but have more versatile possibilities for use, in particular due to the absence of any oil phase which may lead to lighter-colored aqueous gels. They are in the form of powders, but have dissolution times, and thus an ease of implementation, comparable to those of products that are in the form of liquids. They are described in the European patent application published under the number EP 1 496 081 A2. They are obtained via standard polymerization techniques, such as dispersed-phase radical polymerization, inverse suspension radical polymerization, combined inverse emulsion or inverse microemulsion radical polymerization followed by separation via various techniques such as precipitation in an intermediary solvent, precipitation in an intermediary solvent followed by optional washing, drying by atomization or by azeotropic dehydration, optionally followed by washing with an astutely chosen solvent. These synthetic thickeners thus combine some of the advantages of synthetic thickeners that are in the form of standard powders (absence of oil, production of lighter-colored aqueous gels) and the advantages of synthetic thickeners that are in the form of inverse latices (pre-neutralization, high rate of dissolution, noteworthy thickening power and stabilizing properties). However, for uses intended for the preparation of sera as described previously, consumers who use such synthetic thickening systems wish to be able to manufacture gels that are even lighter colored than those obtained at the present time, or even transparent gels. Furthermore, the gels obtained with these synthetic thickeners do not have satisfactory stability when the composition is rich in electrolytes, as is often the case for sera comprising, for example, electrolyte-rich plant extracts or mineral salts.

Linear, branched or crosslinked terpolymers of at least one monomer bearing a free, partially salified or totally salified strong acid function, and at least one monomer of formula (B):

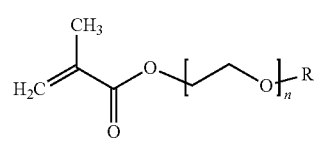

(B)

in which R represents a linear or branched alkyl radical including from 8 to 20 carbon atoms and n represents a number greater than or equal to 1 and less than or equal to 30 are described in the international patent application published under the number WO 2011/030044.

However, when aqueous gels are prepared by implementing such synthetic thickening polymers in the presence of an amount of greater than 0.2% by mass of electrolytes, an aspect which does not meet the transparency requirement associated with the preparation of sera and desired by consumers is always observed.

The inventors thus sought to develop novel aqueous gels which are stable on storage and conserve high viscosity in the presence of electrolyte-rich media and over a wide pH range, and which also conserve satisfactory sensory properties, i.e. which have no tacky or runny nature when they are taken up and after application to the skin, and which have a transparent appearance.

According to a first aspect, a subject of the invention is a composition ($C_1$) comprising, per 100% of its mass:

a)—from 90 mass % to 99.0 mass % of water comprising, in dissolved form, between 0.02 mol and 1 mol per liter and more particularly between 0.02 mol and 0.5 mol per liter of at least one salt (S) of the ammonium cation or of a monovalent or multivalent metal cation (S) with an organic or inorganic anion, b)—from 0.5 mass % to 5 mass % of at least one crosslinked anionic polyelectrolyte (PA) derived from the polymerization, in the presence of at least one crosslinking agent, of partially or totally salified 2-methyl-2-[(1-oxo-2-propenyl)amino]-1-propanesulfonic acid with at least one neutral monomer chosen from N,N-dialkylacrylamides, in which each of the alkyl groups includes between 1 and 4 carbon atoms, and at least one monomer of formula (I):

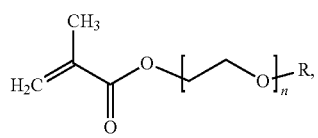
(I)

in which R represents a linear or branched alkyl radical including from 8 to 20 carbon atoms and n represents a number greater than or equal to 1 and less than or equal to 20, and c)—from 0.5 mass % to 5 mass % of at least one compound of formula (II):

(II)

in which $R_1$ represents a saturated or unsaturated, linear or branched hydrocarbon-based aliphatic radical, optionally substituted with one or more hydroxyl groups, including from 12 to 22 carbon atoms, and p represents an integer greater than or equal to 10 and less than or equal to 100, it being understood that in said composition ($C_1$), the mass ratio ($R_a$) between said crosslinked anionic polyelectrolyte (PA) and said compound of formula (II) is greater than or equal to 0.2 and less than or equal to 2.0 and more particularly less than or equal to 1.5 and the mole ratio ($R_b$) between the compound of formula (II) and the salt (S) is greater than or equal to 0.02 and less than or equal to 1 and more particularly greater than or equal to 0.04 and less than or equal to 0.7.

In the definition of the composition ($C_1$) that is a subject of the present invention, the term "crosslinked anionic polyelectrolyte (PA)" denotes a nonlinear crosslinked anionic polyelectrolyte, which is in the form of a three-dimensional network which is insoluble in water but swellable in water and which leads to the production of a chemical gel.

In the definition of the crosslinked anionic polyelectrolyte (PA) present in the composition ($C_1$) as defined above, the term "partially salified or totally salified" means that said 2-methyl-2-[(1-oxo-2-propenyl)amino]-1-propanesulfonic acid is partially or totally salified, especially in the form of an alkali metal salt, for example in the form of a sodium salt or a potassium salt, or in the form of an ammonium salt.

In the definition of the composition ($C_1$) which is a subject of the present invention, the term "neutral monomer chosen from N,N-dialkylacrylamides, in which each of the alkyl groups includes between 1 and 4 carbon atoms" more particularly denotes N,N-dimethylacrylamide, N,N-diethylacrylamide, N,N-dipropylacrylamide, or N,N-diisopropylacrylamide.

According to a particular aspect of the present invention, in composition ($C_1$) as defined above, said crosslinked anionic polyelectrolyte (PA) includes, per 100 mol % of its constituent monomers, from 5 mol % to 95 mol %, more particularly from 10 mol % to 90 mol % and most particularly from 20 mol % to 80 mol % of monomer units derived from partially or totally salified 2-methyl-2-[(1-oxo-2-propenyl)amino]-1-propanesulfonic acid.

According to another particular aspect of the present invention, in composition ($C_1$) as defined above, said crosslinked anionic polyelectrolyte (PA) includes, per 100 mol % of its constituent monomers, from 4.9 mol % to 90 mol %, more particularly from 9.5 mol % to 85 mol %, and most particularly from 15 mol % to 75 mol % of monomer units derived from at least one neutral monomer chosen from N,N-dialkylacrylamides, in which each of the alkyl groups includes between 1 and 4 carbon atoms.

According to another particular aspect of the present invention, in composition ($C_1$) which is a subject of the present invention, said crosslinked anionic polyelectrolyte (PA) includes, per 100 mol % of its constituent monomers, from 0.1 mol % to 10 mol % and more particularly from 0.5 mol % to 5 mol % of monomer units derived from the monomer of formula (I) as defined previously.

A subject of the invention is more particularly a composition ($C_1$) as defined previously, characterized in that said crosslinked anionic polyelectrolyte (PA) includes, per 100 mol % of its constituent monomers:

from 20 mol % to 80 mol % of monomer units derived from partially or totally salified 2-methyl-2-[(1-oxo-2-propenyl)amino]-1-propanesulfonic acid;

from 15 mol % to 75 mol % of monomer units derived from a neutral monomer chosen from N,N-dialkylacrylamides, in which each of the alkyl groups includes between 1 and 4 carbon atoms;

from 0.5 mol % to 5 mol % of monomer units derived from a monomer of formula (I) as defined previously.

According to an even more particular aspect, composition ($C_1$) as defined previously is characterized in that said neutral monomer is N,N-dimethylacrylamide.

In formula (I) as defined previously, the term "linear or branched alkyl radical including from 8 to 20 carbon atoms" more particularly denotes for R:

either a radical derived from a linear primary alcohol chosen, for example, from the octyl, decyl, undecyl, dodecyl, tridecyl, tetradecyl, pentadecyl, hexadecyl, heptadecyl, octadecyl, nonadecyl and eicosyl radicals;

or a radical derived from a Guerbet alcohol, which are branched 1-alkanols corresponding to the general formula:

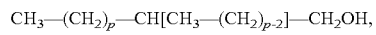

in which p represents an integer between greater than or equal to 3 and less than or equal to 9, chosen, for example, from 2-ethylhexyl, 2-propylheptyl, 2-butyloctyl, 2-pentylnonyl, 2-hexyldecyl and 2-octyldodecyl radicals;

or a radical derived from an isoalkanol corresponding to the general formula:

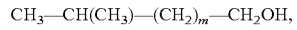

in which m represents an integer greater than or equal to 4 and less than or equal to 16, chosen, for example, from 6-methylheptyl, 15-methylpentadecyl and 16-methylheptadecyl radicals;

or a radical derived from a branched primary alcohol, chosen, for example, from 2-hexyloctyl, 2-octyldecyl and 2-hexyldodecyl radicals.

According to a particular aspect, a subject of the invention is a composition ($C_1$) as defined previously, characterized in that, in the definition of formula (I), R represents an alkyl radical including from 12 to 18 carbon atoms and more particularly a radical chosen from dodecyl, tridecyl, tetradecyl, hexyldecyl, heptadecyl and octadecyl radicals.

According to another particular aspect, a subject of the invention is a composition ($C_1$) as defined previously, characterized in that, in the definition of formula (I), n represents an integer greater than or equal to 3 and less than or equal to 20.

According to an even more particular aspect, composition ($C_1$) as defined previously is characterized in that said monomer of formula (I) is tetraethoxylated lauryl methacrylate.

According to an even more particular aspect, composition ($C_1$) as defined previously is characterized in that said monomer of formula (I) is eicosa-ethoxylated stearyl methacrylate.

According to another particular aspect, a subject of the invention is a composition ($C_1$) as defined previously, characterized in that the crosslinking agent used in the polymerization from which said crosslinked anionic polyelectrolyte (PA) as defined previously is derived is a diethylenic or polyethylenic compound used in a molar proportion, expressed relative to the monomers used, of greater than or equal to 0.005 mol % and less than or equal to 1 mol %, more particularly greater than or equal to 0.01 mol % and less than or equal to 0.5 mol % and most particularly greater than or equal to 0.01 mol % and less than or equal to 0.25 mol %. The crosslinking agent is more particularly chosen from ethylene glycol dimethacrylate, tetraallyloxyethane, ethylene glycol diacrylate, diallylurea, triallylamine, trimethylolpropane triacrylate and methylenebis(acrylamide), or a mixture of these compounds and most particularly chosen from triallylamine, trimethylolpropane triacrylate and methylenebis(acrylamide).

In the polymerization reaction leading to the crosslinked anionic polyelectrolyte (PA) used in composition ($C_1$) which is a subject of the present invention, various additives such as complexing agents, transfer agents or chain-limiting agents may also be used. The transfer agents or chain-limiting agents are more particularly chosen from the group constituted by sodium hypophosphite, alcohols of low molecular weight, for example methanol, ethanol, 1-propanol, isopropanol or butanol, thiols, for example 2-mercaptoethanol, transfer agents comprising a sulfate function, for example sodium methallyl sulfonate, or mixtures of said transfer agents. The transfer agents or chain-limiting agents are more particularly used in molar proportions, expressed relative to the total number of moles of monomers used, of greater than or equal to 0.001 mol % and less than or equal to 1 mol %, more particularly greater than or equal to 0.001 mol % and less than or equal to 0.5 mol %, and most particularly greater than or equal to 0.001 mol % and less than or equal to 0.1 mol %.

In formula (II) as defined previously, the term "saturated or unsaturated, linear or branched aliphatic hydrocarbon-based radical including from 12 to 22 carbon atoms, optionally substituted with one or more hydroxyl groups" denotes, more particularly for $R_1$:

either a saturated linear alkyl radical chosen, for example, from dodecyl, tridecyl, tetradecyl, pentadecyl, hexadecyl, heptadecyl, octadecyl, nonadecyl, eicosyl and docosyl radicals;

or an unsaturated linear radical chosen, for example, from dodecenyl, tridecenyl, tetradecenyl, pentadecenyl, hexadecenyl, heptadecenyl, octadecenyl, nonadecenyl, eicosenyl, docosenyl, 4-dodecenyl and 5-dodecenyl radicals;

or a saturated or unsaturated, linear or branched aliphatic radical including from 12 to 22 carbon atoms substituted with 1 or 2 hydroxyl groups, chosen, for example, from hydroxydodecyl, hydroxytetradecyl, hydroxyhexadecyl, hydroxyoctadecyl, such as the 12-hydroxyoctadecyl radical, hydroxyeicosyl and hydroxydocosyl radicals, or a radical derived from an isoalkanol corresponding to the general formula:

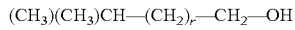

$(CH_3)(CH_3)CH-(CH_2)_r-CH_2-OH$ in which r represents an integer between 8 and 18, chosen, for example, from isododecyl, isotridecyl, isotetradecyl, isopentadecyl, isohexadecyl, isoheptadecyl, isooctadecyl, isononadecyl, isoeicosyl and isodocosyl radicals;

or a branched alkyl radical derived from a Guerbet alcohol, of formula:

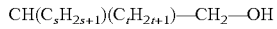

$CH(C_sH_{2s+1})(C_tH_{2t+1})-CH_2-OH$ in which t is an integer between 6 and 18, s is an integer between 4 and 18 and the sum s+t is greater than or equal to 10 and less than or equal to 20, chosen, for example, from 2-butyloctyl, 2-butyldecyl, 2-hexyloctyl, 2-hexyldecyl, 2-octyldecyl, 2-hexyldodecyl and 2-octyldodecyl radicals.

According to another particular aspect, a subject of the invention is a composition ($C_1$) as defined previously, characterized in that, in the definition of formula (II), the radical $R_1$ represents a radical chosen from linear dodecyl, tridecyl, tetradecyl, pentadecyl, hexadecyl, heptadecyl, octadecyl, nonadecyl, eicosanoyl and n-docosyl radicals; and more particularly from dodecyl, tridecyl, tetradecyl, pentadecyl and hexadecyl radicals.

According to another particular aspect, a subject of the invention is a composition ($C_1$) as defined previously, characterized in that, in formula (II), p represents an integer greater than or equal to 15 and less than or equal to 100 and even more particularly an integer greater than or equal to 15 and less than or equal to 50, and even more particularly an integer greater than or equal to 15 and less than or equal to 40.

According to another particular aspect, a subject of the invention is a composition ($C_1$) as defined previously, characterized in that, in formula (II), the radical $R_1$ represents a radical chosen from linear dodecyl, tridecyl, tetradecyl, pentadecyl and hexadecyl radicals and p represents an integer greater than or equal to 15 and less than or equal to 40.

According to a particular aspect, a subject of the invention is a composition ($C_1$) as defined previously, characterized in that said crosslinked anionic polyelectrolyte (PA) is a terpolymer of ammonium 2-methyl-2-[(1-oxo-2-propenyl)amino]-1-propanesulfonic acid, of N,N-dimethylacrylamide and of tetraethoxylated lauryl methacrylate, crosslinked with trimethylolpropane triacrylate.

As a most particular example of such a composition, there is the composition ($C_1$) as defined previously, characterized in that said crosslinked anionic polyelectrolyte (PA) includes, per 100 mol %:

from 60 mol % to 80 mol % of monomer units derived from 2-methyl-2-[(1-oxo-2-propenyl)amino]-1-propanesulfonic acid, partially salified in ammonium form, from 15 mol % to 39.5 mol % of monomer units derived from N,N-dimethylacrylamide, and from 0.5 mol % to 5 mol % of monomer units derived from tetraethoxylated lauryl methacrylate.

In composition ($C_1$) as defined previously, and which is a subject of the present invention, the term "salt (S)" denotes a heteropolar compound whose crystal lattice comprises the participation of at least one type of cation other than hydrogen ions and of at least one type of anion other than hydroxide ions.

According to a more particular aspect, the salt (S), which is in a dissolved form in composition ($C_1$) that is a subject of the present invention, is chosen from inorganic salts and from organic salts.

According to a particular aspect, a subject of the invention is a composition ($C_1$) as defined previously, characterized in that the salt (S) is chosen from inorganic salts and more particularly from halides, carbonates, bicarbonates, phosphates, nitrates, borates and sulfates of ammonium or of a metal cation.

According to a more particular aspect, a subject of the invention is a composition ($C_1$) as defined previously, characterized in that the salt (S) is an inorganic salt whose metal cation is a monovalent or multivalent cation chosen from sodium, potassium, lithium, calcium, magnesium, zinc, manganese, iron, copper, cobalt, silver, gold, aluminum, barium, bismuth, selenium, zirconium, strontium and tin cations.

According to another particular aspect, the salt (S) is particularly chosen from organic salts and more particularly a salt (S) of the ammonium cation or of a monovalent or multivalent metal cation (S) with an organic anion bearing at least one carboxylate, sulfonate or sulfate function.

According to this particular aspect, a subject of the invention is a composition ($C_1$) as defined previously, characterized in that the salt (S) is an organic salt constituted by a monovalent or multivalent metal cation more particularly chosen from elements of the group constituted by sodium, potassium, lithium, calcium, magnesium, zinc, manganese, iron, copper, cobalt, silver, gold, aluminum, barium, bismuth, selenium, zirconium, strontium and tin cations. According to this particular aspect, the salt (S) is an organic salt constituted by the cation chosen from the elements of the group constituted by sodium, calcium, magnesium, zinc and manganese cations, and even more particularly the salt (S) is an organic salt constituted by the sodium cation.

According to another particular aspect, a subject of the invention is a composition (C1) as defined previously, characterized in that the salt (S) is an organic salt constituted by a cation which is the ammonium ion or a metal cation as described previously, and by an organic anion which is an organic compound bearing at least one carboxylic acid function in carboxylate form chosen from the elements of the group constituted by glycolic acid, citric acid, tartaric acid, salicylic acid, lactic acid, mandelic acid, ascorbic acid, pyruvic acid, fumaric acid, retinoic acid, benzoic acid, kojic acid, ellagic acid, malic acid, gluconic acid, sorbic acid, galacturonic acid, propionic acid, dehydroacetic acid, heptanoic acid, 4-aminobenzoic acid, cinnamic acid, benzalmalonic acid, aspartic acid, glutamic acid, glycine, capryloyl glycine, undecylenoyl glycine, undecylenoic acid, phenylalanine, undecylenoyl phenylalanine and hyaluronic acid.

According to an even more particular aspect, a subject of the invention is a composition ($C_1$) as defined previously, characterized in that the salt (S) is chosen from sodium chloride, calcium chloride, magnesium chloride, calcium sulfate, ammonium sulfate, calcium carbonate, zinc sulfate, magnesium sulfate, sodium borate, sodium glycolate, sodium citrate, sodium salicylate, sodium lactate, sodium gluconate, zinc gluconate, manganese gluconate, copper gluconate and magnesium aspartate.

According to another particular aspect, a subject of the invention is a composition ($C_1$) as defined previously, characterized in that the salt (S) is an organic salt constituted by a cation which is the ammonium ion or a metal cation as described previously, and by an organic anion which is an organic compound bearing at least one sulfonic acid function in sulfonate form chosen from the elements of the group constituted by 2-phenylbenzimidazole-5-sulfonic acid, sulfonic acids derived from benzophenones, for instance 4-hydroxy-2-methoxy-5-(oxophenylmethyl)benzenesulfonic acid (said acid being registered under the name Benzophenone-4), sulfonic acids derived from 3-benzylidenecamphor, for instance 4-(2-oxo-3-bornylidenemethyl)benzenesulfonic acid and 2-methyl-5-(2-oxo-3-bornylidenemethyl)benzenesulfonic acid.

According to an even more particular aspect, a subject of the invention is a composition ($C_1$) as defined previously, characterized in that the salt (S) is an organic salt chosen from the elements of the group constituted by sodium 2-phenylbenzimidazole-5-sulfonate and sodium 4-hydroxy-2-methoxy-5-(oxophenylmethyl)benzenesulfonate.

2-Phenylbenzimidazole-5-sulfonic acid is sold especially under the brand name Eusolex™ 232. Sodium 4-hydroxy-2-methoxy-5-(oxophenylmethyl)benzenesulfonate is registered under the name Benzophenone-5.

Composition ($C_1$) according to the invention is prepared by mixing its constituents, with mechanical stirring, at a stirring speed of between 50 rpm and 500 rpm, more particularly between 50 rpm and 100 rpm, at a temperature of between 20° C. and 80° C., more particularly between 20° C. and 60° C. and even more particularly between 20° C. and 45° C.

Composition ($C_1$) which is a subject of the present invention may be packaged in pressurized form in an aerosol device or in a device of "pump-bottle" type, in a device equipped with a perforated wall, for example a grille, or in a device equipped with a ball applicator (known as a "roll-on"). When it is packaged in bottles, composition ($C_1$) according to the invention as defined previously may be applied in the form of fine droplets by means of mechanical pressurization devices or via a propellant gas. Among the propellants that may be combined with composition ($C_1$) according to the invention are hydrofluoro compounds, for instance dichlorodifluoromethane, trichlorofluoromethane, difluoroethane, isobutane, butane and propane.

Composition ($C_1$) as defined previously may also include excipients and/or active principles commonly used in the field of formulations for topical use, in particular cosmetic, dermocosmetic, pharmaceutical or dermopharmaceutical formulations.

This is why, according to another particular mode, a subject of the invention is a composition ($C_1$) as defined previously, characterized in that it also comprises one or more auxiliary compounds chosen from foaming and/or detergent surfactants, thickening and/or gelling surfactants, thickeners and/or gelling agents, stabilizers, film-forming compounds, solvents and cosolvents, hydrotropic agents, plasticizers, opacifiers, nacreous agents, sequestrants, chelating agents, antioxidants, fragrances, essential oils, preserving agents, conditioning agents, deodorants, bleaching agents intended for bleaching bodily hair and the skin, active principles intended to provide a treating and/or protective action to the skin or the hair, sunscreens, mineral fillers or pigments, particles that give a visual effect or that are intended for encapsulating active agents, exfoliant particles, texture agents, optical brighteners and insect repellents.

Among the volatile solvents that may be combined with composition ($C_1$) according to the invention are volatile water-soluble alcohols, for instance ethanol, isopropanol or butanol, and more particularly ethanol, organic solvents such as glycerol, diglycerol, glycerol oligomers, 1,2-propanediol, 1,3-propanediol, 1,3-butanediol, 1,4-butanediol, 1,6-hexanediol, 2-methyl-2,4-pentanediol, 1,2-pentanediol, 2-methyl-1,3-propanediol, 2-methyl-2,4-pentanediol (or hexylene glycol), dipropylene glycol, xylitol, erythritol and sorbitol. According to a particular aspect, composition ($C_1$) according to the invention comprises, per 100% of its mass, up to 20% by mass of one or more volatile solvents chosen from ethanol, isopropanol, butanol, 1,3-propanediol, 1,3-butanediol, 2-methyl-2,4-pentanediol, xylitol and sorbitol.

According to another particular aspect, composition ($C_1$) according to the invention does not comprise any volatile solvents.

According to another particular aspect, composition ($C_1$) according to the invention is a hydrogel.

Among the water-soluble antioxidants that may be combined with composition ($C_1$) according to the invention are ascorbic acid, glutathione, tartaric acid, oxalic acid and tetrasodium glutamate diacetate.

Among the water-soluble sequestrants that may be combined with composition ($C_1$) according to the invention are ethylenediaminetetraacetic acid (EDTA) salts, for instance the sodium salt of EDTA, and diethylenetriaminepentaacetic acid (DTPA) salts, for instance the sodium salts of DTPA.

Among the water-soluble dyes that may be combined with composition ($C_1$) according to the invention are caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, cochineal carmine (CI 15850, CI 75470), Ext. Violet 2, Red 6-7, Ferric Ferrocyanide, Ultramarines, Acid yellow 3/Yellow 10, Acid Blue 3, Yellow 10.

Among the color-stabilizing water-soluble agents that may be combined with composition ($C_1$) according to the invention are tris(tetramethylhydroxypiperidinol) citrate, sodium benzotriazolyl butylphenol sulfonate and benzotriazolyl dodecyl p-cresol.

As examples of foaming and/or detergent surfactants optionally present in composition ($C_1$) which is a subject of the present invention, mention may be made of topically acceptable anionic, cationic, amphoteric or nonionic foaming and/or detergent surfactants commonly used in this field of activity.

Among the foaming and/or detergent anionic surfactants that may be combined with composition ($C_1$) which is a subject of the present invention, mention may be made of alkali metal salts, alkaline-earth metal salts, ammonium salts, amine salts, amino alcohol salts of alkyl ether sulfates, of alkyl sulfates, of alkylamido ether sulfates, of alkylarylpolyether sulfates, of monoglyceride sulfates, of α-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkylsulfosuccinates, of alkyl ether sulfosuccinates, of alkylamide sulfosuccinates, of alkyl sulfoacetates, of alkyl sarcosinates, of acylisethionates, of N-acyl taurates, of acyl lactylates, of N-acylamino acid derivatives, of N-acyl peptide derivatives, of N-acyl protein derivatives or of fatty acids.

Among the foaming and/or detergent amphoteric surfactants optionally present in composition ($C_1$) which is a subject of the present invention, mention may be made of alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants optionally present in composition ($C_1$) which is a subject of the present invention, mention may be made particularly of quaternary ammonium derivatives.

Among the foaming and/or detergent nonionic surfactants optionally present in composition ($C_1$) which is a subject of the present invention, mention may be made more particularly of alkylpolyglycosides comprising a linear or branched, saturated or unsaturated aliphatic radical and comprising from 8 to 12 carbon atoms; castor oil derivatives, polysorbates, coconut kernel amides and N-alkylamines.

As examples of texture agents optionally present in composition ($C_1$) which is a subject of the present invention, mention may be made of N-acylamino acid derivatives, for example lauroyl lysine sold under the name Aminohope™LL, octenyl starch succinate sold under the name Dryflo™, myristyl polyglucoside sold under the name Montanov™ 14, cellulose fibers, cotton fibers, chitosan fibers, talc, sericite, mica and perlite.

Examples of active principles optionally present in composition ($C_1$) that is a subject of the present invention include:
vitamins and derivatives thereof, for example retinol (vitamin A) and esters thereof (for example retinyl palmitate), ascorbic acid (vitamin C) in the form of the salts and esters thereof, sugar derivatives of ascorbic acid (for example ascorbyl glucoside), tocopherol (vitamin E) and esters thereof (for example tocopheryl acetate), vitamins B3 or B10 (niacinamide and derivatives thereof);
compounds with a lightening or depigmenting action on the skin, for example Sepiwhite™ MSH, arbutin, kojic acid, hydroquinone, Vegewhite™, Gatuline™, Synerlight™, Biowhite™, Phytolight™, Dermalight™, Clariskin™, Melaslow™, Dermawhite™, Ethioline, Melarest™, Gigawhite™, Albatine™ and Lumiskin™;
compounds with a calmative action, such as Sepicalm™ S, allantoin and bisabolol;
anti-inflammatory agents;
compounds with moisturizing action, for example diglycerol, triglycerol, urea, hydroxyureas, glycerol glucoside, diglycerol glucoside, polyglyceryl glucosides, erythrityl glucoside, sorbityl glucoside, xylityl glucoside, the composition sold under the brand name Aquaxyl™ comprising xylityl glucoside, anhydroxylitol and xylitol;
compounds with slimming or lipolytic action, such as caffeine or derivatives thereof, Adiposlim™ and Adipoless™;
N-acyl proteins; N-acyl peptides, for example Matrixil™; N-acyl amino acids; partial hydrolyzates of N-acyl proteins; amino acids; peptides; total protein hydrolyzates;
plant extracts rich in tannins, polyphenols and/or isoflavones, for example grape extracts, pine extracts, wine extracts, olive extracts; soybean extracts, for example Raffermine™; wheat extracts, for example Tensine™ or Gliadine™; terpene-rich rich plant extracts; freshwater or seawater algal extracts; marine extracts in general such as corals;

compounds with antimicrobial action or with purifying action, for example Lipacide™ C8G, Lipacide™ UG, Sepicontrol™ A5; Octopirox™ or Sensiva™ SC50;

compounds with an energizing or stimulating property, such as Physiogenyl™, panthenol and derivatives thereof such as Sepicap™ MP;

antiaging active agents such as Sepilift™ DPHP, Lipacide™ PVB, Sepivinol™, Sepivital™, Manoliva™, Phyto-Age™, Timecode™ or Survicode™;

active agents for combating photoaging;

active agents for increasing the synthesis of extracellular matrix components, for example collagen, elastins and glycosaminoglycans;

active agents acting favorably on chemical cellular communication, such as cytokines, or physical cellular communication, such as integrins;

active agents which create a "heating" sensation on the skin, such as skin capillary circulation activators (for example nicotinic acid derivatives) or products which create a "freshness" sensation on the skin (for example menthol and derivatives thereof);

active agents which improve the skin capillary circulation, for example venotonic agents; draining active agents; decongesting active agents, for example extracts of *Ginkgo biloba*, ivy, common horse chestnut, bamboo, ruscus, butcher's-broom, broom, *Centella asiatica*, fucus, rosemary or willow;

active agents acting as skin-tautening agents, for example plant protein hydrolyzates, hydrolyzates of marine origin, for instance hydrolyzates of laminaria extracts, fish cartilage hydrolyzates, marine elastin, the product sold by the company SEPPIC under the brand name Sesaflash™, and collagen solutions;

skin tanning or browning agents, for example dihydroxyacetone, isatin, alloxan or ninhydrin, glyceraldehyde, mesotartaric aldehyde, glutaraldehyde or erythrulose.

As examples of deodorants optionally present in composition ($C_1$) which is a subject of the present invention, mention may be made of alkali metal silicates, zinc salts such as zinc sulfate, zinc gluconate, zinc chloride or zinc lactate; quaternary ammonium salts such as cetyltrimethylammonium salts or cetylpyridinium salts; glycerol derivatives such as glyceryl caprate, glyceryl caprylate and polyglyceryl caprate; 1,2-decanediol; 1,3-propanediol; salicylic acid; sodium bicarbonate; cyclodextrins; metallic zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

As examples of sunscreens optionally present in composition ($C_1$) which is a subject of the present invention, mention may be made of all those listed in the modified cosmetics directive 76/768/EEC, annex VII.

A subject of the invention is also the use of composition ($C_1$) as described previously, as a topical cosmetic composition for cleansing and/or protecting and/or caring for the skin and/or for improving and/or preserving the esthetic appearance of the skin, the hair or mucous membranes.

The word "topical" used in the definition of composition ($C_1$) means, for the purposes of the present patent application, that said composition ($C_1$) is used by application to the skin, the scalp or mucous membranes, whether this is a direct application in the case of a cosmetic, dermocosmetic, dermopharmaceutical or pharmaceutical formulation or an indirect application, for example in the case of a product for bodily hygiene or for caring for or protecting the skin, in the form of a textile article, for instance a wipe, or a paper article, for instance a paper for sanitary use.

According to a more particular aspect, when composition ($C_1$) that is a subject of the present invention is used for cleansing the skin, the hair or the scalp, it also comprises at least one detergent surfactant.

According to another more particular aspect, composition ($C_1$) that is a subject of the present invention may be used for caring for or protecting the skin, for example against solar radiation, or for preventing aging of the skin, or alternatively as a cosmetic product for treating acne and/or blackheads and/or comedones or as a moisturizing product.

A subject of the invention is also a process for lightening a composition comprising at least 90% by mass of water, said water comprising, in dissolved form, between 0.02 mol and 1 mol per liter of at least one salt (S) of the ammonium cation or of a monovalent or multivalent metal cation (S) with an organic or inorganic anion, and at least one crosslinked anionic polyelectrolyte (PA) derived from the polymerization, in the presence of at least one crosslinking agent, of partially or totally salified 2-methyl-2-[(1-oxo-2-propenyl)amino]-1-propanesulfonic acid, with at least one neutral monomer chosen from N,N-dialkylacrylamides, in which each of the alkyl groups includes between 1 and 4 carbon atoms, and at least one monomer of formula (I):

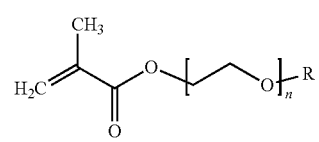

(I)

in which R represents a linear or branched alkyl radical including from 8 to 20 carbon atoms and n represents a number greater than or equal to 1 and less than or equal to 20, said process comprising a step of adding to said composition an effective amount of at least one compound of formula (II):

$$R_1-(O-CH_2-CH_2)_p-OH \quad (II),$$

in which $R_1$ represents a saturated or unsaturated, linear or branched hydrocarbon-based aliphatic radical, optionally substituted with one or more hydroxyl groups, including from 12 to 22 carbon atoms, and p represents an integer greater than or equal to 10 and less than or equal to 100, such that said composition comprises, on conclusion of this step and per 100% of its mass, a)—from 90 mass % to 99.0 mass % of water comprising, in dissolved form, between 0.02 mol and 1 mol per liter of at least one salt (S) of the ammonium cation or of a monovalent or multivalent metal cation (S) with an organic or inorganic anion, b)—from 0.5 mass % to 5 mass % of said compound of formula (I), c)—from 0.5 mass % to 5 mass % of said compound of formula (II), it being understood that the mass ratio ($R_a$) between said crosslinked anionic polyelectrolyte (PA) and said compound of formula (II) is greater than or equal to 0.2 and less than or equal to 2.0 and that the mole ratio ($R_b$) between the compound of formula (II) and the salt (S) is greater than or equal to 0.02 and less than or equal to 1.

For the purposes of the present invention, the term "lightening" refers to a visual modification of the appearance of said composition, which is reflected by the obtention of a turbidity value for composition ($C_1$) of less than or equal to 25 NTU, measured at a temperature of 25° C. and using a DRT 100B model optical turbidimeter sold by the company HF Scientific, calibrated beforehand with a formazine solution (0.9 NTU).

In the definition of the process as defined above, the term "effective amount of the compound of formula (II)" denotes a mass amount of the compound of formula (II) such that the final composition obtained via said process:

has a turbidity value of less than or equal to 25 NTU, measured at a temperature of 25° C. and using a DRT 100B model optical turbidimeter sold by the company HF Scientific, calibrated beforehand with a formazine solution (0.9 NTU), and has a dynamic viscosity of greater than or equal to 100 mPa·s and less than or equal to 50 000 mPa·s, said dynamic viscosity being measured using a Brookfield viscometer, of LV type, at a spin speed of 6 rpm and at a temperature of 25° C.±2° C., and remains homogeneous after storage for three months at a temperature of 25° C.

The following experimental study illustrates the invention without, however, limiting it.

I—PREPARATION OF CROSSLINKED ANIONIC POLYELECTROLYTES

I-1 Terpolymer of mmonium 2-methyl-2-[(1-oxo-2-propenyl)amino]-1-propanesulfonate, N,N-dimethylacrylamide and tetraethoxylated lauryl methacrylate [AMPSNH$_4$/DMAM/LMA (4 EO) 77.4/19.2/3.4 molar], Crosslinked with trimethylolpropane triacrylate (TMPTA).

592 g of an aqueous solution containing 15% by mass of ammonium 2-methyl-2-[(1-oxo-2-propenyl)amino]-1-propanesulfonate (AMPSNH$_4$) in a tert-butanol/water mixture (97.5/2.5 by volume), 10.1 g of N,N-dimethylacrylamide (DMAM), 4.2 g of tetraethoxylated lauryl methacrylate [LMA (4 EO)] and 0.75 g of TMPTA are placed in a reactor maintained at 25° C. with stirring. After a sufficient time to achieve good homogenization of the solution, it is deoxygenated by sparging with nitrogen heated to 70° C. 0.42 g of dilauroyl peroxide is then added and the reaction medium is then maintained for approximately 60 minutes at 70° C. and then for 2 hours at 80° C. After cooling, the powder which has formed during polymerization is filtered off and dried to obtain the desired product, hereinafter referred to as: "Polyelectrolyte (PA)".

II—PREPARATION AND EVALUATION OF AQUEOUS COMPOSITIONS ACCORDING TO THE INVENTION AND OF COMPARATIVE AQUEOUS COMPOSITIONS

II-1 Preparation of the Aqueous Compositions According to the Invention 14 aqueous compositions according to the invention, named ($E_1$) to ($E_{14}$), are prepared, the mass proportions of the constituents of which are indicated in table 1.

The preparation process common to these 14 compositions is as follows:

the required amount of water is poured into a reactor equipped with mechanical stirring and a jacket comprising a heat-exchange fluid, at a temperature of 20° C., and is then brought to a temperature of 75° C. with mechanical stirring at a speed of 80 rpm;

the crosslinked anionic polyelectrolyte (PA) is then gradually added at this temperature of 75° C. with mechanical stirring;

after homogenization of the gel obtained previously, the solubilizing agent of formula (II) to be tested is then gradually added at the temperature of 75° C. with mechanical stirring at a speed of 80 rpm;

the mixture obtained is then cooled to a temperature of 40° C., and the salt (S) and the preserving agent are then added to the medium obtained previously, with continued mechanical stirring at a speed of 80 rpm.

TABLE 1

| Composition | ($E_1$) | ($E_2$) | ($E_3$) | ($E_4$) |
|---|---|---|---|---|
| Polyelectrolyte (PA) (mass %) | 2.25 | 2.25 | 0.50 | 1 |
| Sodium chloride (S) (mol/liter) | 0.34 | 0.34 | 0.34 | 0.34 |
| Euxyl ™ PE9010[1] (mass %) | 1 | 1 | 1 | 1 |
| Simulsol ™ P23[2] (II) (mass %) | 2.50 | 0 | 2.50 | 2.50 |
| Simulsol ™ 58[3] (II) (mass %) | 0 | 2.50 | 0 | 0 |
| Water | qs100% | qs100% | qs100% | qs100% |
| $R_a$ = (PA)/(II) (by mass) | 0.90 | 0.90 | 0.20 | 0.40 |
| $R_b$ = (II)/(S) (molar) | 0.06 | 0.07 | 0.06 | 0.06 |

| Composition | ($E_5$) | ($E_6$) | ($E_7$) | ($E_8$) |
|---|---|---|---|---|
| Polyelectrolyte (PA) (mass %) | 1.75 | 3.00 | 2.25 | 2.25 |
| Sodium chloride (S) (mol/liter) | 0.34 | 0.34 | 0.34 | 0.34 |
| Euxyl ™ PE9010[1] (mass %) | 1 | 1 | 1 | 1 |
| Simulsol ™ P23[2] (II) (mass %) | 2.50 | 2.50 | 1.50 | 2.000 |
| Water | qs100% | qs100% | qs100% | qs100 |
| $R_a$ = (PA)/(II) (by mass) | 0.70 | 1.20 | 1.50 | 1.13 |
| $R_b$ = (II)/(S) (molar) | 0.06 | 0.06 | 0.04 | 0.05 |

| Composition | ($E_9$) | ($E_{10}$) | ($E_{11}$) | ($E_{12}$) |
|---|---|---|---|---|
| Polyelectrolyte (PA) (mass %) | 2.25 | 2.25 | 2.25 | 2.25 |
| Sodium chloride (S) (mol/liter) | 0.34 | 0.34 | 0.034 | 0.08 |
| Euxyl ™ PE9010[1] (mass %) | 1 | 1 | 1 | 1 |
| Simulsol ™ P23[2] (II) (mass %) | 3.0 | 5.0 | 2.50 | 2.50 |
| Water | qs 100% | qs 100% | qs 100% | qs 100% |
| $R_a$ = (PA)/(II) (by mass) | 0.75 | 0.45 | 0.9 | 0.9 |
| $R_b$ = (II)/(S) (molar) | 0.07 | 0.12 | 0.61 | 0.24 |

| Composition | ($E_{13}$) | ($E_{14}$) |
|---|---|---|
| Polyelectrolyte (PA) (mass %) | 2.25 | 2.25 |
| Sodium chloride (S) (mol/liter) | 0.17 | 0.26 |
| Euxyl ™ PE9010[1] (mass %) | 1 | 1 |
| Simulsol ™ P23[2] (II) (mass %) | 2.50 | 2.50 |
| Water | qs 100% | qs 100% |
| $R_a$ = (PA)/(II) (by mass) | 0.9 | 0.9 |
| $R_b$ = (II)/(S) (molar) | 0.12 | 0.08 |

[1]Euxyl ™ PE9010 is a mixture of phenoxyethanol and ethylhexylglycerol;
[2]Simulsol ™ P23 is a lauryl alcohol ethoxylated with 23 mol of ethylene oxide (MW = 1198);
[3]Simulsol ™ 58 is a palmityl alcohol ethoxylated with 20 mol of ethylene oxide (MW = 1122).

II-2 Preparation of the Comparative Aqueous Compositions

Eight comparative aqueous compositions, named ($F_1$) to ($F_8$), are prepared, the mass proportions of the constituents of which are indicated in table 2.

The preparation process common to these eight compositions is as follows:

the required amount of water is poured into a reactor equipped with mechanical stirring and a jacket comprising a heat-exchange fluid, at a temperature of 20° C., and is then brought to a temperature of 75° C. with mechanical stirring at a speed of 80 rpm;

the crosslinked anionic polyelectrolyte (PA) is then gradually added at this temperature of 75° C. with mechanical stirring;

after homogenization of the gel obtained previously, the solubilizing agent of formula (II') to be tested is then gradually added at the temperature of 75° C. with mechanical stirring at a speed of 80 rpm;

the mixture obtained is then cooled to a temperature of 40° C., and the salt (S) and the preserving agent are then added to the medium obtained previously, with continued mechanical stirring at a speed of 80 rpm.

TABLE 2

| Composition | ($F_1$) | ($F_2$) | ($F_3$) | ($F_4$) |
|---|---|---|---|---|
| Polyelectrolyte (PA) (mass %) | 2.25 | 2.25 | 2.25 | 2.25 |
| Sodium chloride (S) (mol/liter) | 0.34 | 0.34 | 0.34 | 0.34 |
| Euxyl ™ PE9010[1] (mass %) | 1 | 1 | 1 | 1 |
| Montanox ™ 20[4] (II') (mass %) | 0 | 2.50 | 0 | 0 |
| Simulsol ™ 1292[5] (II') (mass %) | 0 | 0 | 2.50 | 0 |
| Oramix ™ CG 110[6] (II') (mass %) | 0 | 0 | 0 | 2.50 |
| Water | qs100% | qs100% | qs100% | qs100% |
| $R'_a$ = (PA)/(II') (by mass) | NA | 0.9 | 0.9 | 0.9 |
| $R'_b$ = (II')/(S) (molar) | ND | 0.06 | ND | ND |

| Composition | ($F_5$) | ($F_6$) | ($F_7$) | ($F_8$) |
|---|---|---|---|---|
| Polyelectrolyte (PA) (mass %) | 2.25 | 2.25 | 2.25 | 2.25 |
| Sodium chloride (S) (mol/liter) | 0.34 | 0.34 | 0.34 | 0.34 |
| Euxyl ™ PE9010[1] (mass %) | 1 | 1 | 1 | 1 |
| Sepiclear ™ G7[7] | 2.5 | 0 | 0 | 0 |
| Simulsol ™ P7[8] (mass %) | 0 | 2.50 | 0 | 0 |
| Simulsol ™ P23[2] (II) (mass %) | 0 | 0 | 0.50 | 1 |
| Water | Qs. 100% | Qs. 100% | Qs. 100% | Qs. 100% |
| $R'_a$ = (PA)/(II') (by mass) | 0.9 | 0.9 | 4.5 | 2.25 |
| $R'_b$ = (II')/(S) (molar) | ND | 0.14 | 0.012 | 0.024 |

[4]Montanox ™ 20 is a sorbitan monolaurate ethoxylated with 20 mol of ethylene oxide (MW = 1226);
[5]Simulsol ™ 1292 (INCI name: PEG-25 hydrogenated castor oil) is a hydrogenated castor oil ethoxylated with 25 mol of ethylene oxide;
[6]Oramix ™ CG 110 is an aqueous composition comprising caprylyl glucoside and capryl glucoside.
[7]Sepiclear ™ G7 is an aqueous composition comprising n-heptyl glucoside;
[8]Simulsol ™ P7 is a lauryl alcohol ethoxylated with 7 mol of ethylene oxide.

II-3 Demonstration of the Properties and Characteristics of the Aqueous Compositions According to the Invention and of the Comparative Aqueous Compositions The aqueous compositions ($E_1$) to ($E_{14}$) according to the invention and the comparative compositions ($F_1$) to ($F_8$) thus prepared are then stored in an insulated climatic chamber regulated at a temperature of 25° C., for 7 days. On conclusion of this period of 7 days, each aqueous composition is evaluated by the following measurements:

measurement of the dynamic viscosity (μ) at 25° C. using a Brookfield LVT viscometer at a speed of 6 rpm (V6), equipped with a suitable spindle, after a period of storage of 7 days at 25° C.;

measurement of the turbidity of the aqueous composition obtained at a temperature of 25° C., using an HF Scientific™, model DRT100B optical turbidimeter, calibrated beforehand with a formazine solution (0.9 NTU); the turbidity measurements are expressed in NTU units;

visual evaluation of the appearance of the aqueous composition prepared after a period of storage of three months at 25° C.; the visual appearance of each aqueous composition is noted by the experimenter and qualified as clear (L), cloudy (T) or cloudy-heterogeneous (T-H), depending on the case.

The results obtained for the aqueous compositions ($E_1$) to ($E_{14}$) according to the invention and the comparative compositions ($F_1$) to ($F_8$) are collated, respectively, in tables 3 and 4 below.

TABLE 3

| Compositions | ($E_1$) | ($E_2$) | ($E_3$) | ($E_4$) | ($E_5$) |
|---|---|---|---|---|---|
| Visual appearance after 7 days at 25° C. | L | L | L | L | L |
| Visual appearance after 3 months at 25° C. | L | L | L | L | L |
| μ after 7 days at 25° C. | 8300 | 8400 | 100 | 155 | 3000 |
| Turbidity (NTU) | 11 | 14 | 14 | 15 | 20 |

| Compositions | ($E_6$) | ($E_7$) | ($E_8$) | ($E_9$) | ($E_{10}$) |
|---|---|---|---|---|---|
| Visual appearance after 7 days at 25° C. | L | L | L | L | L |
| Visual appearance after 3 months at 25° C. | L | L | L | L | L |
| μ after 7 days at 25° C. | 22 700 | 10 600 | 9700 | 7300 | 5500 |
| Turbidity (NTU) | 24 | 11 | 13 | 12 | 23 |

| Compositions | ($E_{11}$) | ($E_{12}$) | ($E_{13}$) | ($E_{14}$) |
|---|---|---|---|---|
| Visual appearance after 7 days at 25° C. | L | L | L | L |
| Visual appearance after 3 months at 25° C. | L | L | L | L |
| μ after 7 days at 25° C. | 21 800 | 15 400 | 15 100 | 12 900 |
| Turbidity (NTU) | 19 | 24 | 20 | 15 |

TABLE 4

| Compositions | ($F_1$) | ($F_2$) | ($F_3$) | ($F_4$) |
|---|---|---|---|---|
| Visual appearance after 7 days at 25° C. | T | T | T | T |
| Visual appearance after 3 months at 25° C. | T | T | T | T-H |
| μ after 7 days at 25° C. | 58 000 | 15 000 | 9500 | 20 000 |
| Turbidity (NTU) | >500 | >150 | >150 | >150 |

| Compositions | ($F_5$) | ($F_6$) | ($F_7$) | ($F_8$) |
|---|---|---|---|---|
| Visual appearance after 7 days at 25° C. | T | T | T | T |
| Visual appearance after 3 months at 25° C. | T | T | T | T |
| μ after 7 days at 25° C. | 25 500 | 40 000 | 20 000 | 14 340 |
| Turbidity (NTU) | >150 | 65 | 155 | 52 |

II-4 Analysis of the Results a) The use of solubilizing agents known to those skilled in the art, for instance Polysorbate 20, hydrogenated castor oil ethoxylated with 25 mol of ethylene oxide, caprylyl/capryl glucoside or n-heptyl glucoside, which are respectively present in the comparative compositions ($F_2$), ($F_3$), ($F_4$) and ($F_5$), does not make it possible to sufficiently and satisfactorily lighten a thickened aqueous composition, comprising a mass amount of 2% of sodium chloride, represented by composition ($F_1$). Specifically, the comparative compositions ($F_2$), ($F_3$), ($F_4$) and ($F_5$), differing only in the nature of the solubilizing agent, do not make it possible to reach a turbidity value of less than 100 NTU.

b) The use as solubilizing agent of a lauryl alcohol ethoxylated with 23 mol of ethylene oxide and of a palmityl alcohol ethoxylated with 20 mol of ethylene oxide, which are respectively present in compositions ($E_1$) and ($E_2$), makes it possible to sufficiently and satisfactorily lighten a thickened aqueous composition, comprising a mass amount of 2% of sodium chloride, represented by composition ($F_1$), whereas the use of a lauryl alcohol ethoxylated with 7 mol of ethylene oxide in composition ($F_6$) does not make it possible to obtain sufficient and satisfactory lightening. Specifically, compositions ($E_1$) and ($E_2$) according to the invention are characterized by a turbidity value of 11 NTU and 14 NTU, respectively, whereas the turbidity of the comparative composition ($F_6$) is equal to 65 NTU.

c) Compositions ($E_3$) to ($E_{14}$) according to the invention show the obtention of turbidity values of less than 25 NTU, for various values of the mass ratio $R_a$ and the mole ratio $R_b$ as defined previously, with various mass proportions of the ingredients concerned. The comparative compositions ($F_7$) and ($F_8$) show that when at least one of the ratios $R_a$ or $R_b$ is not within the required value ranges, the lightening afforded is insufficient and unsatisfactory. Specifically, in the case of the comparative composition ($F_7$), the value of the mass ratio $R_a$ is established at 4.5, the value of the mole ratio $R_b$ established at 0.012 and the turbidity value of composition ($F_7$) is measured at 155 NTU. Similarly, in the case of the comparative composition ($F_8$), the value of the mass ratio $R_a$ is established at 2.25 and the turbidity value of composition ($F_8$) is measured at 52 NTU.

Placing in perspective the results obtained for compositions ($E_1$) to ($E_{14}$) according to the invention and the comparative compositions ($F_1$) to ($F_8$) clearly reveals that the lightening of thickened, salt-rich aqueous compositions, conserving a sufficient level of viscosity, could not be deduced from the results associated with the aqueous compositions of the prior art.

III—DRAINING AND REFRESHING FLUID FOR HEAVY LEGS

| | Formula | |
|---|---|---|
| A | Sepinov ™ EMT10 | 0.75% |
| | Polyelectrolyte ($PA_1$) | 0.75% |
| | Glycerol | 2% |
| | Water | qs 100% |
| B | Simulsol 58 | 4% |
| C | Ethanol | 20% |
| | Sculptosane | 1% |
| | Euxyl K701 | 1% |
| | Essential oil of peppermint | 0.25% |
| | Essential oil of Siberian cypress | 0.25% |

Procedure:

Sepinov™ EMT10 and the polyelectrolyte ($PA_1$) are dispersed in the mixture of water and glycerol brought beforehand to a temperature of 75° C., with mechanical stirring using a turbomixer of rotor-stator type, at a speed of 2000 rpm until a homogeneous gel is obtained. Phase B is then gradually added to the aqueous gel obtained beforehand, with mechanical stirring at a speed of 1500 rpm. The mixture is then cooled to a temperature of 40° C., phase C is then gradually added and the formulation obtained is then homogenized for 30 minutes at room temperature.

The commercial products used in the examples are defined as follows:

Sepinov™ EMT 10 (INCI name: Hydroxyethyl acrylate/sodium acryloyldimethyltaurate copolymer) is a thickening polymer sold by the company SEPPIC;

Sculptosane (INCI name: Aqua (and) Butylene Glycol (and) Plankton Extract (and) Arginine Ferulate) is a water-soluble plankton extract with densifying properties on the skin's epidermis, sold by the company SEPPIC;

Euxyl™K702 (INCI name: Benzoic Acid, Dehydroacetic Acid, Phenoxyethanol, Polyaminopropyl Biguanide and Ethylhexylglycerin) is a mixture used as a preserving agent, sold by the company SEPPIC.

The invention claimed is:

1. A composition ($C_1$) comprising, per 100% of its mass:
a)—from 90 mass % to 99 mass % of water comprising, in dissolved form, between 0.02 mol and 1 mol per liter of at least one salt (S) of an ammonium cation or of a monovalent or multivalent metal cation (S) with an organic or inorganic anion,
b)—from 0.5 mass % to 5 mass % of at least one crosslinked anionic polyelectrolyte (PA) derived from the polymerization, in the presence of at least one crosslinking agent, of partially or totally salified 2-methyl-2-[(1-oxo-2-propenyl)amino]-1-propanesulfonic acid with at least one neutral monomer chosen from N,N-dialkylacrylamides, in which each of the alkyl groups includes between 1 and 4 carbon atoms, and at least one monomer of formula (I):

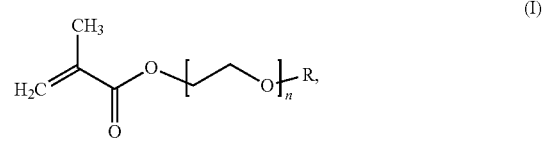

in which R represents a linear or branched alkyl radical including from 8 to 20 carbon atoms and n represents a number greater than or equal to 1 and less than or equal to 20, and
c)—from 0.5 mass % to 5 mass % of at least one compound of formula (II):

in which $R_1$ represents a saturated or unsaturated, linear or branched hydrocarbon-based aliphatic radical, substituted with one or more hydroxyl groups, including from 12 to 22 carbon atoms, and p represents an integer greater than or equal to 10 and less than or equal to 100, it being understood that, in said composition ($C_1$), the mass ratio ($R_a$) between said at least one crosslinked anionic polyelectrolyte (PA) and said at least one compound of formula (II) is greater than or equal to 0.2 and less than or equal to 2.0 and that the mole ratio ($R_b$) between the at least one compound of formula (II) and the at least one salt (S) is greater than or equal to 0.02 and less than or equal to 1.

2. The composition ($C_1$) as defined in claim 1, wherein said at least one crosslinked anionic polyelectrolyte (PA) comprises, per 100 mol % of its constituent monomers:

from 20 mol % to 80 mol % of monomer units derived from partially or totally salified 2-methyl-2-[(1-oxo-2-propenyl)amino]-1-propanesulfonic acid;

from 15 mol % to 75 mol % of monomer units derived from a neutral monomer chosen from N,N-dialkylacrylamides, in which each of the alkyl groups includes between 1 and 4 carbon atoms;

from 0.5 mol % to 5 mol % of monomer units derived from a monomer of formula (I) as defined previously.

3. The composition ($C_1$) as defined in claim 2, wherein said neutral monomer is N,N-dimethylacrylamide.

4. The composition ($C_1$) as defined in claim 3, wherein said monomer of formula (I) is tetraethoxylated lauryl methacrylate.

5. The composition ($C_1$) as defined in claim 3, wherein, in formula (II), the radical $R_1$ represents a radical chosen from linear dodecyl, tridecyl, tetradecyl, pentadecyl and hexadecyl radicals and p represents an integer greater than or equal to 15 and less than or equal to 40.

6. The composition ($C_1$) as defined in claim 2, wherein said monomer of formula (I) is tetraethoxylated lauryl methacrylate.

7. The composition ($C_1$) as defined in claim 2, wherein, in formula (II), the radical $R_1$ represents a radical chosen from linear dodecyl, tridecyl, tetradecyl, pentadecyl and hexadecyl radicals and p represents an integer greater than or equal to 15 and less than or equal to 40.

8. The composition ($C_1$) as defined in claim 1, wherein said at least one monomer of formula (I) is tetraethoxylated lauryl methacrylate.

9. The composition ($C_1$) as defined in claim 8, wherein, in formula (II), the radical $R_1$ represents a radical chosen from linear dodecyl, tridecyl, tetradecyl, pentadecyl and hexadecyl radicals and p represents an integer greater than or equal to 15 and less than or equal to 40.

10. The composition ($C_1$) as defined in claim 1, wherein, in formula (II), the radical $R_1$ represents a radical chosen from linear dodecyl, tridecyl, tetradecyl, pentadecyl and hexadecyl radicals and p represents an integer greater than or equal to 15 and less than or equal to 40.

11. The composition ($C_1$) as defined in claim 1, wherein said at least one crosslinked anionic polyelectrolyte (PA) is a terpolymer of 2-methyl-2-[(1-oxo-2-propenyl)amino]-1-propanesulfonic acid, partially salified in ammonium salt form, of N,N-dimethylacrylamide and of tetraethoxylated lauryl methacrylate, crosslinked with trimethylolpropane triacrylate.

12. The composition ($C_1$) as defined in claim 1, wherein said at least one crosslinked anionic polyelectrolyte (PA) includes, per 100 mol %:

from 60 mol % to 80 mol % of monomer units derived from 2-methyl-2-[(1-oxo-2-propenyl)amino]-1-propanesulfonic acid, partially salified in ammonium form, from 15 mol % to 39.5 mol % of monomer units derived from N,N-dimethylacrylamide, and from 0.5 mol % to 5 mol % of monomer units derived from tetraethoxylated lauryl methacrylate.

13. The composition ($C_1$) as defined in claim 1, wherein said at least one salt (S) is chosen from halides, carbonates, bicarbonates, phosphates, nitrates, borates and sulfates of an ammonium cation or of a metal cation.

14. The composition ($C_1$) as defined in claim 1, wherein said at least one salt (S) is a salt (S) of an ammonium cation or of a monovalent or multivalent metal cation (S) with an organic anion bearing at least one chosen from carboxylate, sulfonate and sulfate functions.

15. The composition ($C_1$) as defined in claim 1, wherein said at least one salt (S) is chosen from sodium chloride, calcium chloride, magnesium chloride, calcium sulfate, ammonium sulfate, calcium carbonate, zinc sulfate, magnesium sulfate, sodium borate, sodium glycolate, sodium citrate, sodium salicylate, sodium lactate, sodium gluconate, zinc gluconate, manganese gluconate, copper gluconate and magnesium aspartate.

16. The composition ($C_1$) as defined in claim 1, further comprising one or more auxiliary compounds chosen from foaming and/or detergent surfactants, thickening and/or gelling surfactants, thickeners and/or gelling agents, stabilizers, film-forming compounds, solvents and cosolvents, hydrotropic agents, plasticizers, opacifiers, nacreous agents, sequestrants, chelating agents, antioxidants, fragrances, essential oils, preserving agents, conditioning agents, deodorants, bleaching agents intended for bleaching bodily hair and the skin, active principles intended to provide a treating and/or protective action to the skin or the hair, sunscreens, mineral fillers or pigments, particles that give a visual effect or that are intended for encapsulating active agents, exfoliant particles, texture agents, optical brighteners and insect repellents.

17. A topical cosmetic composition for cleansing and/or protecting and/or caring for the skin and/or for improving and/or preserving the esthetic appearance of the skin, the hair or mucous membranes, comprising the composition of claim 1.

18. A process for lightening a composition comprising at least 90% by mass of water, said water comprising, in dissolved form, between 0.02 mol and 1 mol per liter of at least one salt (S) of an ammonium cation or of a monovalent or multivalent metal cation (S) with an organic or inorganic anion, and at least one crosslinked anionic polyelectrolyte (PA) derived from the polymerization, in the presence of at least one crosslinking agent, of partially or totally salified 2-methyl-2-[(1-oxo-2-propenyl)amino]-1-propanesulfonic acid, with at least one neutral monomer chosen from N,N-dialkylacrylamides, in which each of the alkyl groups includes between 1 and 4 carbon atoms, and at least one monomer of formula (I):

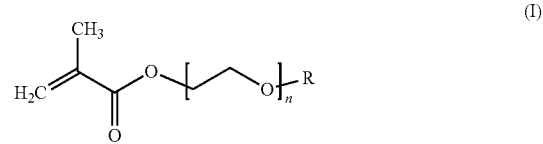

(I)

in which R represents a linear or branched alkyl radical including from 8 to 20 carbon atoms and n represents a number greater than or equal to 1 and less than or equal to 20, said process comprising a step of adding to said composition an effective amount of at least one compound of formula (II):

$R_1$—(O—CH$_2$—CH$_2$)$_p$—OH (II), in which $R_1$ represents a saturated or unsaturated, linear or branched hydrocarbon-based aliphatic radical, substituted with one or more hydroxyl groups, including from 12 to 22 carbon atoms, and p represents an integer greater than or equal to 10 and less than or equal to 100, such that said composition comprises, on conclusion of this step and per 100% of its mass, a)—from 90 mass % to 99 mass % of water comprising, in dissolved form, between 0.02 mol and 1 mol per liter of said at least one salt (S) of an ammonium cation or of a monovalent or multivalent metal cation (S) with an organic or inorganic anion,
b)—from 0.5 mass % to 5 mass % of said at least one crosslinked anionic polyelectrolyte (PA),
c)—from 0.5 mass % to 5 mass % of said compound of formula (II), it being understood that the mass ratio ($R_a$) between said at least one crosslinked anionic polyelectrolyte (PA) and said at least one compound of formula (II) is greater than or equal to 0.2 and less than or equal to 2.0 and the mole ratio ($R_b$) between the at least one compound of formula (II) and the at least one salt (S) is greater than or equal to 0.02 and less than or equal to 1.

* * * * *